United States Patent [19]

Stineman et al.

[11] 4,192,918

[45] Mar. 11, 1980

[54] PRODUCTION OF BAKER'S YEAST FROM ACID WHEY

[75] Inventors: Thomas L. Stineman; Jeffrey D. Edwards, both of Cincinnati, Ohio; Jack C. Grosskopf, Wheaton, Ill.

[73] Assignee: The Kroger Co., Cincinnati, Ohio

[21] Appl. No.: 964,990

[22] Filed: Nov. 30, 1978

[51] Int. Cl.$^2$ .......................... C12N 1/18; C12C 11/08
[52] U.S. Cl. ...................................... 435/256; 426/41; 426/60; 210/2; 210/11; 435/942
[58] Field of Search ...................... 195/13, 27, 40, 41, 195/82, 83; 426/41, 60; 210/2, 11

[56] References Cited

U.S. PATENT DOCUMENTS

| | | | |
|---|---|---|---|
| 3,818,109 | 6/1974 | Bechtle et al. | 195/82 X |
| 3,968,257 | 7/1976 | Muller | 426/41 |

*Primary Examiner*—Lionel M. Shapiro
*Attorney, Agent, or Firm*—Cushman, Darby & Cushman

[57] ABSTRACT

Acid whey, the by-product from the manufacture of fresh cheeses such as cottage cheese, is clarified, filtered and subjected to lactose hydrolysis, splitting the lactose disaccharide into the monosaccharides glucose and galactose. The liquid is sterilized and cultured with Baker's yeast and used as a growth medium for that yeast. After yeast growth is substantially completed the yeast solids are separated and the liquid remaining is discharged into waste-water receiving systems, the liquid significantly reduced in organic waste loading as compared to untreated acid wheys.

9 Claims, No Drawings

PRODUCTION OF BAKER'S YEAST FROM ACID WHEY

BACKGROUND OF THE INVENTION

This application relates to a process for treating acid whey, a by-product from the manufacture of cottage cheese or other fresh cheeses, and converting it into a valuable product while at the same time avoiding the customary high organics discharge into waste water treatment systems.

Cheese whey is reported to be the largest single by-product of the dairy industry. This whey is customarily discharged into municipal sewage systems which creates a most difficult disposal problem as most cheese plants are located in urban areas. It contains about half of the nutritive value of the milk from which the cheese is produced and, in the case of acid whey from cottage cheese manufacture, it contains levels of lactose sugar, protein, lactic acid and mineral salts. Cheese whey disposal is a difficult problem from the standpoint of pollution due to the organic nutrients contained therein and it has been estimated that as compared to domestic waste water, a quantity of one thousand gallons per day of raw whey discharged into a municipal sewage system can impose a load about equal to that generated by one thousand, eight hundred people.

While the solids of sweet whey are much more readily utilized as an animal or human food material than those of acid wheys, the acid wheys represent the major portion of the liquid wheys which are not being utilized. As an indication of the volume of acid wheys which are generated, acid wheys are produced in the making of cottage cheese, cream cheese, baker's cheese, neufchatel cheese, ricotta cheese and other fresh cheeses as distinguished from aged cheeses like cheddar cheese and swiss cheese.

The problem of whey disposal is substantial, particularly in view of the fact that many municipal treatment facilities which process the discharged whey are making substantial surcharges to the cheese processors. Indeed, concern exists as to the continued availability of municipal treatment facilities in many areas to accept and process discharged whey, notwithstanding the treatment charges and surcharges which are applied.

As will be apparent from the conditions outlined above, there exists a substantial need for a convenient, cost-effective process or procedure for the processing of whey discharge fluids. The dairy industry has considered various approaches for the treatment of cheese wheys, especially acid wheys, and a review of some of these proposals is given in Wix and Woodbine, *Dairy Sci. Absts.* 18:537-548 and 621-630. Various procedures have been described in the patent literature as well, including converting whey solids to an edible yeast cell mass in which the protein and carbohydrate content of cheese whey is converted substantially entirely to yeast cells as described in U.S. Pat. No. 3,818,109 and various publications mentioned therein. Fermentative utilization of whey has been proposed which, in theory, provides a means for increasing the nutritive value of the whey as compared to dried whey products, and yeasts in particular have been considered as fermentative agents. However, such procedures have not reached a point of practical application.

Prior to the present invention, insofar as we are aware there has not been developed a commercially practical method for the treatment of acid whey, substantially eliminating the organic waste loads which it represents, and essentially converting the acid whey into a commercially useful yeast product. Where the objective is to produce a synthetic bread flavor, it has been proposed that pasteurized whey substrates of 6 to 40% solids can be fermented with a yeast, such as *Saccharomyces cerevisiae* (Baker's yeast), and a coccus bacteria, such as an enterococcus of serological group D, to produce lactic acid in situ. This is necessary since Baker's yeast is capable of utilizing lactic acid but not lactose. Instead of the bacteria, lactic acid can be added directly. The medium is aerated during fermentation for a growth period of up to 24 hours. A nitrogen source, such as diammonium phosphate, may be added to the whey medium. (See Bundus, et al U.S. Pat. Nos. 3,466,174 and 3,466,176). In the Bundus, et al. process, only part of the whey proteins and lactose are utilized, and the process is terminated with the substrate containing about 5% by volume of yeast together with whey protein and lactose thus not substantially eliminating the organics content of the discharged product as is the object of the present invention. Preferably, as described in U.S. Pat. No. 3,466,176, the whey protein is subjected to a high heat treatment before being utilized in the process, which is said to enhance the development of the desired bread flavor. Apparently, this is due to partial heat denaturation of the whey protein which inhibits some of the utilization of the protein by the growing yeast.

The process of the present invention is distinguished from the Bundus et al type of process in such features as the whey treatment procedures, sugars hydrolysis, fermentation and nature of the product produced, among others.

BRIEF DESCRIPTION OF THE INVENTION

A process is disclosed for treating acid whey, the by-product of the manufacture of fresh cheeses, such as cottage cheese, converting a significant portion thereof into a yeast product and substantially or completely eliminating objectionable organic waste loads which are discharged into waste water treatment systems. Other objects and advantages of the present invention will be apparent from the following disclosure and examples.

DETAILED DESCRIPTION OF THE INVENTION

According to the disclosed process, acid whey, the by-product from the manufacture of fresh cheeses, primarily cottage cheese, is first clarified to remove suspended solids, filtered to separate protein and then the remaining liquid, devoid of protein and suspended solids, subjected to lactose hydrolysis. This splits the lactose disaccharide into its component glucose and galactose sugars. The liquid is then sterilized and the pH adjusted to about 5.0 and then fermented, either on a continuous or batch basis, by the addition of a yeast culture. Generally Baker's yeast is used. Once fermentation is complete, the mixture is centrifuged and the yeast solids are separated from the whey, the whey is discharged, and the yeast product is isolated. The thus-processed whey which remains is discharged directly into waste-water receiving systems with an approximate 90% decrease in the organic waste loads that would be present without treatment.

Acid whey, the by-product from the manufacture of cottage cheese and similar cheeses as described above, consists primarily of water, a relatively low level (as calculated against the water content) of lactose, some suspended protein particles, lactic acid and various salts. As an example, 1000 grams of acid whey may be composed of water (950 g), lactose (45 g), potassium (1 g), sodium (0.5 g) and various amounts of protein. The milk protein contained in the whey can be recovered from the whey using various techniques including commercially available ultrafiltration membranes or other means. Protein recovery is a desirable and economical objective. There remains after protein removal quantities of lactose which present the major disposal problems associated with acid whey dairy plant effluents.

The process of the present invention is to utilize the lactose and mineral salts which are present in the deproteinized acid whey as a growth source for a yeast, conveniently and usually Baker's yeast (*Saccharomyces cerevisiae*). Baker's yeast does not grow on the disaccharide lactose but grows readily on the monosaccharides glucose and galactose, components of lactose. The present invention includes splitting the disaccharide linkage of the lactose to free the glucose and galactose for use as the growth medium for the yeast. Conveniently this hydrolysis step is accomplished with one of several commercially available and effective enzymes or enzyme systems, as will be described in further detail below. The enzyme hydrolysis can represent a critical step in the process of the present invention fron an economic viewpoint.

Baker's yeast, a product resulting from the process of the present invention, is itself a recognized and important animal feed supplement; see U.S. Pat. Nos. 2,322,320 and 3,186,922. It is also used in the baking of breads and other bakery products. Baker's yeast is regarded as having a high nutritional value rich in essential amino acids and having a high protein content.

The processing sequence, conditions and details are as follows, it being understood that such are illustrative, but not necessarily limiting, of the present invention.

1. Clarification—A source of acid whey, such as provided directly from the manufacture of cottage cheese, is processed to remove suspended, small cottage cheese or cheese-type particles. A solids separator is typically used and the recovered solids are used in other food processing which itself is not relevant to the present invention.

2. Ultrafiltration—The partially deproteinized whey treated in step 1 is heat treated, for example at 77° C.–80° C. for about 30 seconds, passed through at least one commercially available ultrafiltration membrane, and preferably a series of such membranes, and the protein thus recovered is also used in further food processing, as above. This step is itself known in the art. Various suppliers of ultrafiltration equipment include Abcor, Romicon and DeDanske Sukker fabrikker (D.D.S).

3. Lactose hydrolysis—The lactose-containing portion of the whey permeate from step 2 is next hydrolyzed to split the connecting bond between the glucose and galactose sugars. There are several procedures currently available or in a stage of development which are fully acceptable for the hydrolysis step. As a rule, one will select a particular procedure or system that is not only economically justified but is also compatible with overall dairy processing operations. Accordingly, the following are illustrative procedures and reagents:

(a) Soluble $\beta$—galactosidase enzyme, a lactose, available from Miles Pharmaceutical, Marschall Division, under the designation Miles Fungal Lactase.

(b) Immobilized lactase enzyme which is a $\beta$-galactosidase enzyme immobilized on porous ceramic beads available from Corning Glass Company, Industrial Biologics Division.

(c) Immobilized lactase enzyme which is a $\beta$-galactosidase bound within various commercially available ultrafiltration membranes said to be available from Romicon, Incorporated.

(d) Cation ion exchange resins which split the lactose, sometimes referred to as ion exchange catalyzed hydrolysis. Other fully acceptable techniques will be apparent to one skilled in the art such those proposed by Haggett, *N.Z. Jl Dairy Sci. Technol.*, 11, 176–179 (1976).

4. Fermentation—The thus-hydrolyzed whey permeate, which now contains glucose and galactose, is sterilized by suitable means. Preferred is treatment by heating the whey permeate to a sterilizing temperature, or ultra-violet irradiation. The sterile whey permeate is adjusted to a suitable yeast-growing pH, which in the case of the preferred inoculum is in the range of about pH 5 by addition of ammonia salts. The whey permeate is next inoculated with a culture of *Saccharomyces cerevisiae*. Fully acceptable fermentation conditions include temperatures in the range of about 28° C. to about 32° C., a pH in the range of about 4.60 to about 5.20 and a dilution rate less than about 0.240. The dilution rate refers primarily to a continuous type of fermentation, as described below, and is equal to the volume of whey substrate supplied to the continuous fermentor apparatus divided by the liquid capacity of the fermentor apparatus.

Fermentation may be either continuous or batch-type; for the purposes of the present invention and for economy a continuous fermentation technique is preferred. Using such a procedure, sterilized whey permeate and yeast inoculum are continuously introduced into a yeast growth zone in a reactor and the fermentor liquid is continuously harvested and transferred to storage tanks where it is held under aerated, temperature-controlled conditions for a suitable period of time, approximately four hours. The holding period provides for substantially complete carbohydrate utilization that increases trehalose and protein levels in the yeast culture.

5. Yeast-whey separator—The yeast product is separated from the virtually exhausted whey through continuous centrifuges and the yeast is recovered and used as such, such as in the making of bread and bakery products. The spent whey is discharged to a municipal waste treatment system or other waste water receiving area with an approximate 90% decrease in the organic waste load from the original loading levels.

The continuous fermentation technique is particularly suited to the process of the present invention. Batch fermentation procedures typically involve filling a large container with the nutrient medium, inoculating and growing the yeast with incremental feeding, emptying the container when growth is complete or nearly so, and harvesting the yeast. The container must be re-sterilized before the next filling, large containers are required for substantial yeast production and the entire batch process is labor intensive. By contrast, a continuous fermentation technique requires smaller equipment and is more convenient to operate. As an example, a relatively small, ultra-sterile fermentation vessel is filled with the processed whey liquid, the yeast is inoculated and grown to a high population and additional sterile whey permeate is added as required. At the same time an equal volume of liquid whey plus yeast is removed from the continuous fermentor thus maintaining an even volume in the tank. Yeast is separated from the whey in the manner described above.

The invention will be further explained in the following illustrative examples. Unless otherwise indicated all parts and percentages are by weight.

EXAMPLE 1

Acid whey (1,000 gallons) was clarified to remove the suspended solids and curd particles of the cheese. These solids thus separated may be added to various food products. The clarified whey was next heat-treated at 80° C. for 30 seconds and the protein (approximately 0.5%) was removed by membrane ultrafiltration. The retenate from the membranes amounted to 70 gallons of protein material and 930 gallons of lactose permeate.

The whey proteins contained in the 70 gallons of protein retenate can either be concentrated or can be used as is. The 70 gallons of retenate contained 10% protein and 5% lactose by weight together with low levels of inorganic salts and lactic acid the balance being water. These proteins are very high in nutritive value and are used in various food products.

The membrane permeate (containing 5% lactose by weight together wit minor amounts of inorganic nitrogen, vitamins, salts and lactic acid) was mixed thoroughly in a tank and the temperature maintained at 51° C. Lactase enzyme (commercially available from Miles) was added to the liquid in a concentration of 0.19 grams of enzyme to 1 gallon of permeate to hydrolyze the disaccharide bond in lactose and yield glucose and galactose at levels of 80% of the available monosaccharides.

The hydrolysate (930 gallons) was supplemented with a nitrogen source in the form of diammonium and mono-ammonium phosphate (3.78 grams of both forms per gallon) as well as ammonium sulfate (3.78 grams per gallon of hydrolysate) and vitamin supplements of biotin and thiamine (22.0 milligrams of thiamine hydrochloride and 185 micrograms of D-biotin per gallon of hydrolysate). Also added was inositol at levels of 0.02 grams per gallon of hydrolysate.

This liquid is adjusted to a pH of 5.00 with ammonium hydroxide and sterilized with ultraviolet light, then cooled to 30° C.

A portion of the hydrolysate (200 gallons) was fed into a continuous fermentation reactor, maintained at 30° C., agitated vigorously (about 500 rpm), and aerated at a level above 1 volume of air/volume of liquid/minute (1 V.V.M.).

The reactor was inoculated with a pure culture of *Saccharomyces cerevisiae* and the culture allowed to grow for 18 hours. The inoculum was prepared in the laboratory by inoculating a small amount of cells of *S. cerevisiae* into 2 liters of sterile Wort Liquid (commercially available from Difco Laboratories). This was incubated for 24 hours at 30° C. and this liquid is inoculated into a 10 gallon laboratory fermentor filled with sufficient volume of basal media. The cells of *Saccharomyces cerevisiae* were allowed to grow under aerated conditions at 30° C. for 24 hours before adding it to the larger continuous fermentation reactor.

After the continuous reactor is inoculated and allowed to grow for the specified time, hydrolysate is fed to the reactor at a rate of 39 gallons/hour and the pH of the reactor is maintained at 5.00.

At the same time, liquid substrate containing Baker's yeast was removed from the fermentor at a rate of 39 gallons per hour. This fermented substrate so removed was maintained at a pH of 5.00, aerated with 1 V.V.M. of air and supplied with nitrogen as required for a period of at least 5 hours.

The Baker's yeast was removed from the liquid by centrifugation and dried to a moisture level of 70% on a drum filter with a final yield of yeast of 130 grams per gallon of hydrolyzed whey fermented. This Baker's yeast was then added to bread dough to raise it and give it the proper texture and flavor prior to the baking of the bread.

The fermentation reactor can be maintained by processing additional acid whey in the manner illustrated above, and a continuous process maintained.

The spent, fermented whey (approximately 900 gallons) has a reduced Biochemical Oxygen Demand (B.O.D.) of approximately 90% and may either be discharged to the sewage treatment system or may be used in further processing.

EXAMPLE 2

Acid whey (1,000 gallons) is clarified to remove cottage cheese fines and suspended solids and heat-treated in the manner of Example 1. The pH of the whey is adjusted to 3.50 by adding 4.00 gallons of hydrochloric acid and the protein is removed by membrane ultrafiltration. The membrane retenate containing protein may be dried further or used as is in further food processing.

The membrane permeate (930 gallons) containing lactose as described in Example 1 is fed continuously through a column reactor (approximate size 0.35 M × 2.5 M) containing approximately 57 Kg of Corning Immobilized Lactase Enzyme. The temperature of the permeate is maintained at about 35° C. and the feed rate of permeate through the column is maintained at a flow sufficient to obtain 80% hydrolysis of the lactose into glucose and galactose.

The hydrolysate is sterilized by heating to 90° C. for 30 seconds and then cooled to 30° C.

This sterilized hydrolysate is then supplemented with nitrogen salts and vitamins as described in Example 1, and the pH adjusted to 5.00 with ammonium hydroxide.

This liquid is fermented continuously as described in Example 1 and the Baker's yeast is recovered in the same manner as previously described.

The spent fermented whey (approximately 900 gallons) will be reduced in organic load with an approximate reduction of 90% in B.O.D. and may either be used in further processing or discharged to sewage systems.

EXAMPLE 3

A quantity of acid whey (1000 gallons) was clarified to remove small particles of cheese and suspended solids. These fines may be used in further food processing.

The whey was heat-treated at 80° C. for 30 seconds and cooled to 51° C. The protein portion was removed by ultrafiltration. The membrane retenate (as described in Example 1) containing a nutritive protein may be dried or used as is in further food processing.

The membrane permeate (approximately 930 gallons) containing lactose, trace minerals, salts, and vitamins was mixed thoroughly in a tank and the temperature maintained at 51° C. Lactase enzyme (B-galactosidase available from Miles Marschall Division as Miles Fungal Lactase) was added to the lactose permeate in a concentration of 0.19 grams of enzyme per gallon of permeate to hydrolyze the disaccharide bond in lactose and yield the monosaccharides of glucose and galactose at levels of 70% of the available sugars.

The hydrolysate (930 gallons) was sterilized by ultra-violet light, cooled to 30° C., and supplemented with nitrogen and vitamins in the same manner as described in Example 1. The hydrolysate was added to a large batch fermentation reactor and was inoculated with a pure culture of *Saccharomyces cerevisiae*. The inoculum may be prepared as in Example 1. The temperature of the fermentor was maintained at 30° C., the pH at 5.00; the liquid was aerated at 1 V.V.M. and nitrogen added incrementally as needed. The fermentation in this case was carried out in a traditional batch manner for Baker's yeast as described in Harrison and Rose, *The Yeasts*, Vol. 3, 1971, as well as numerous other sources. (Reed and Pepplar, *Yeast Technology*, 1973).

After the fermentation was complete the fermentation reactor was emptied and the yeast recovered by centrifugation. The yeast (approximately 150 grams per gallon of hydrolysate fermented) was dried to a 70% moisture level on a drum filter. The Baker's yeast then is added to bread dough to raise it and give it the flavor and texture desired in the baking of bread.

The spent whey (slightly less than 900 gallons) indicates a reduction in the B.O.D. of at least 90% and may be used for further processing or discharged directly to sewage systems.

What is claimed is:

1. A process for treating acid whey liquid which contains suspended solids, proteins, lactose and water from the manufacture of fresh cheeses to reduce the organic nutrient content thereof, said process comprising the steps of:
   (a) clarifying acid whey liquid to remove any suspended cheese particles contained therein and separating the thus-removed particles;
   (b) filtering the clarified liquid and separating any remaining protein, leaving an acid whey substantially completely devoid of proteins and suspended solids;
   (c) subjecting the acid whey liquid from step (b) to hydrolysis conditions thereby converting the lactose disaccharide present in the whey liquid into the corresponding glucose and galactose monosaccharides;
   (d) sterilizing the acid whey liquid of step (c);
   (e) adjusting the pH of the sterile liquid to about pH 5 then inoculating the sterile liquid with a culture of *Saccharomyces cerevisiae* yeast and maintaining the thus-inoculated liquid under yeast growth conditions at a temperature of about 28° C. to about 32° C. for a period of time until the glucose and galactose are substantially completely consumed by the yeast growth; and
   (f) separating and removing the yeast produced in step (e) and discharging the remaining liquid.

2. The process as claimed in claim 1, wherein the acid whey liquid is deproteinized in step (b) by heating to a temperature of about 77° C. to about 80° C.

3. The process as claimed in claim 2, wherein the acid whey liquid is passed through at least one ultrafiltration membrane.

4. The process as claimed in claim 1, wherein hydrolysis step (c) is conducted using a lactase enzyme.

5. The process as claimed in claim 4, wherein the lactase enzyme is a soluble $\beta$-galactoside enzyme.

6. The process as claimed in claim 4, wherein the lactase enzyme is an immobilized galactosidase enzyme.

7. The process as claimed in claim 1, wherein a cation exchange resin is employed for said hydrolysis.

8. The process as claimed in claim 1, wherein the inoculated liquid is maintained at a pH of about 4.60 to about 5.20.

9. A process for growing Baker's yeast using treated acid whey as the growth medium and substantially reducing the organic nutrient content of the acid whey, said acid whey composed of water, lactose, suspended protein particles, lactic acid and inorganic salts, said process including the sequential steps of:
   A. clarifying the acid whey liquid by removing any particles suspended therein;
   B. filtering the clarified acid whey liquid and removing protein remaining therein producing a treated acid whey liquid substantially completely devoid of proteins and suspended solids;
   C. hydrolyzing the lactose disaccharide present in the acid whey liquid into the component glucose and galactose monosaccharides;
   D. subjecting the hydrolyzed acid whey liquid of step B to sterilization conditions and sterilizing the liquid;
   E. inoculating the sterile liquid with a yeast culture of *Saccharomyces cerevisiae* and maintaining the inoculated liquid in a continuous fermentation zone under yeast growth conditions until a substantial quantity of yeast is produced in the liquid;
   F. continuously withdrawing at least a portion of the yeast-rich liquid from the containers fermentation zone;
   G. continuously supplying additional sterile liquid to the fermentation zone, the rate of withdrawal and the rate of supply being substantially equal so as to continuously maintain yeast growth conditions in said fermentation zone; and
   H. separating and recovering the yeast contained in the withdrawn liquid, and discharging any remaining liquid.

* * * * *